United States Patent
Jackson (12)

(10) Patent No.: US 6,258,090 B1
(45) Date of Patent: Jul. 10, 2001

(54) CLOSURE FOR OPEN ENDED MEDICAL IMPLANT AND REMOVAL TOOL

(76) Inventor: Roger P. Jackson, 6600 Indian La., Mission Hills, KS (US) 66208

( * ) Notice: Subject to any disclaimer, the term of this patent is extended or adjusted under 35 U.S.C. 154(b) by 0 days.

(21) Appl. No.: 09/561,455

(22) Filed: Apr. 28, 2000

(51) Int. Cl.[7] .................................................. A61B 17/56
(52) U.S. Cl. ............................................... 606/61; 606/72
(58) Field of Search .................................. 606/61, 60, 62, 606/63, 64, 65, 70, 71, 72, 73, 104, 69; 623/17.11, 17.16, 17.17

(56) References Cited

U.S. PATENT DOCUMENTS

| | | |
|---|---|---|
| 5,005,562 | 4/1991 | Cotrel . |
| 5,067,955 | 11/1991 | Cotrel . |
| 5,129,388 | 7/1992 | Vignaud et al. . |
| 5,154,719 | 10/1992 | Cotrel . |
| 5,257,993 | 11/1993 | Asher et al. . |
| 5,261,907 | 11/1993 | Vignaud et al. . |
| 5,261,912 * | 11/1993 | Frigg ...................................... 606/61 |
| 5,346,493 | 9/1994 | Stahurski et al. . |
| 5,385,583 | 1/1995 | Cotrel . |
| 5,487,742 | 1/1996 | Cotrel . |
| 5,562,663 | 10/1996 | Wisnewski et al. . |
| 5,643,260 | 7/1997 | Doherty . |
| 5,697,929 | 12/1997 | Mellinger . |
| 5,725,527 * | 3/1998 | Biedermann et al. .................. 606/61 |
| 5,863,293 * | 1/1999 | Richelson ............................... 606/61 |
| 6,077,262 * | 6/2000 | Schlapfer et al. ....................... 606/61 |
| 6,077,263 * | 6/2000 | Ameil et al. ............................ 606/61 |
| 6,139,549 * | 10/2000 | Keller ..................................... 606/61 |

FOREIGN PATENT DOCUMENTS

WO94/10927 5/1994 (WO) .

OTHER PUBLICATIONS

*Spine*, Lipcott, Williams & Wilkins, Inc., vol. 24, No. 15, p. 1495.

* cited by examiner

Primary Examiner—Pedro Philogene
(74) Attorney, Agent, or Firm—John C. McMahon

(57) ABSTRACT

A closure for use with an open headed medical implant with a pair of inwardly threaded arms. The closure is bow-tie-shaped having a pair of opposed cylindrical sections that have outwardly threaded surfaces that are discontinuous therebetween. The cylindrical surfaces are joined by walls having outer curved surfaces each having a radius that is less than a radius associated with the cylindrical surfaces. The closure also has a central bore receiving a set screw in use. Tools for installing the closure include a tool with a head having a channel receiving the closure and wings on opposite sides of the channel that have outer surfaces that are threaded so as to compliment and complete the threads on the outside of the closure, when the tool is thereon, so as to provide a substantially continuous circumferential thread for installation. A group of removal tools includes a first tool having a head that fits over the closure and includes a pair of wings with outer cam surfaces thereon for operably wedging apart the implant arms and a second non-threaded tool for turning the closure once the arms are wedged apart.

16 Claims, 3 Drawing Sheets

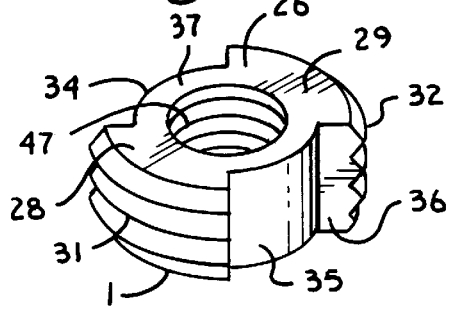
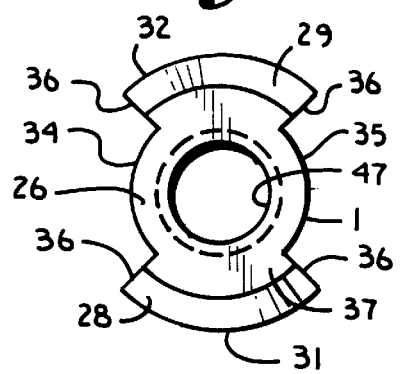
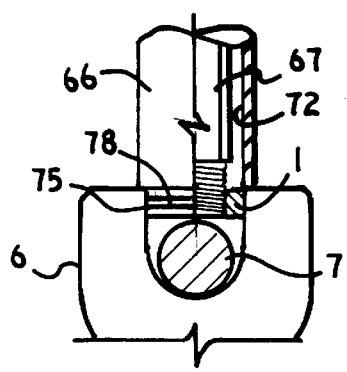
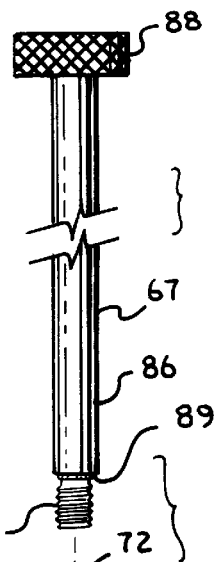
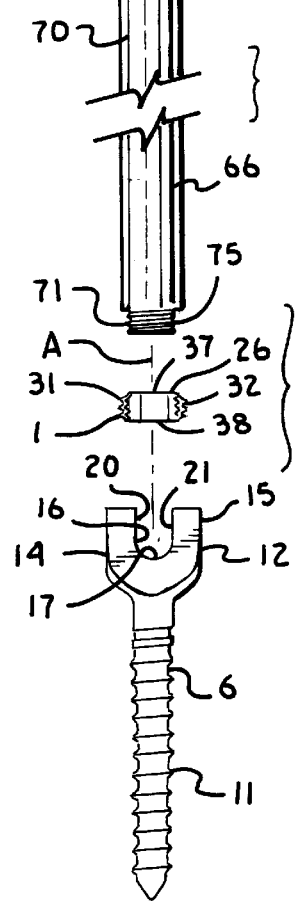

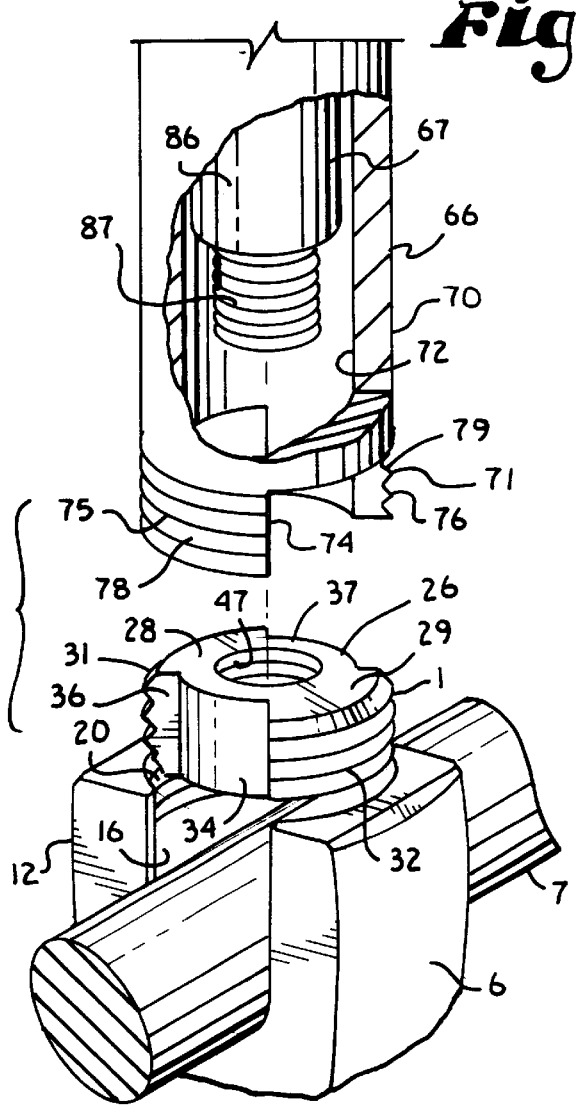
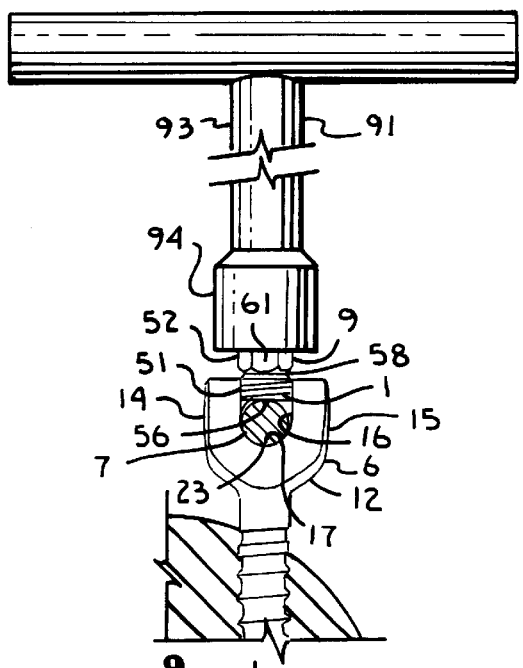
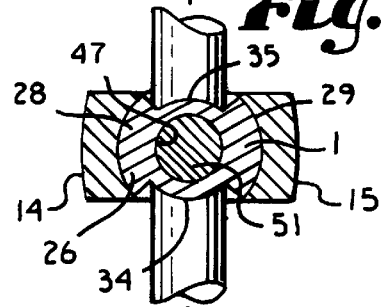
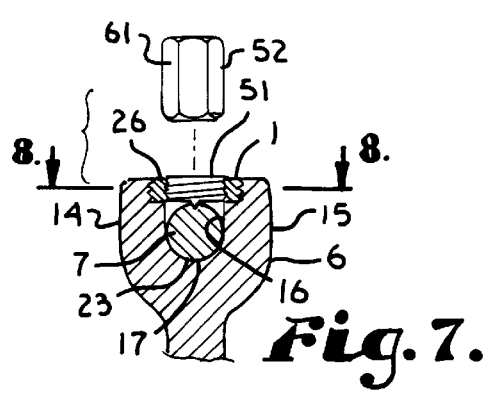
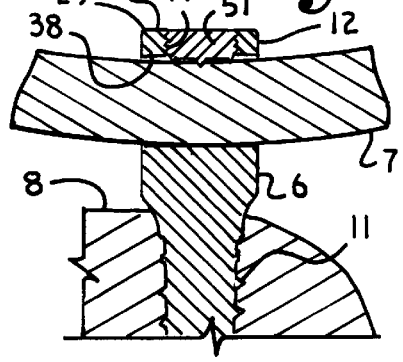

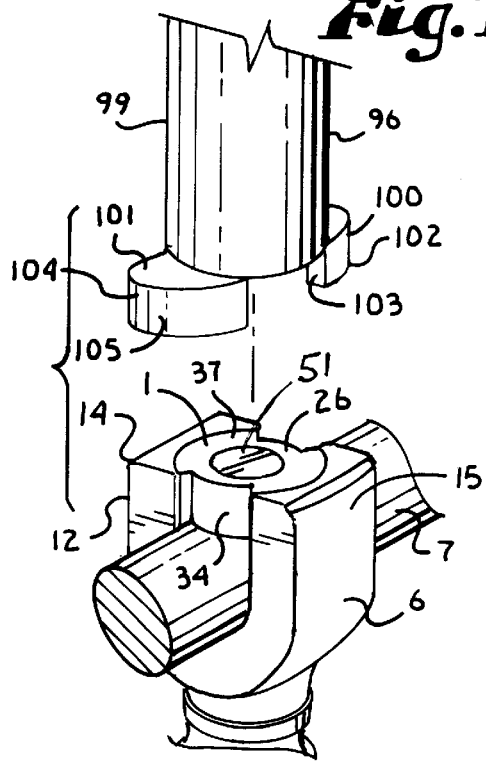
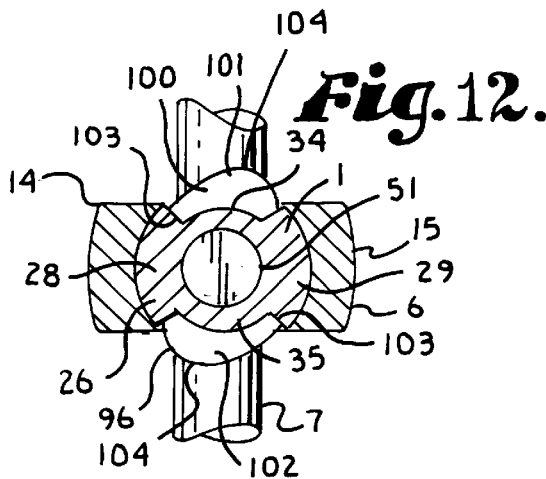
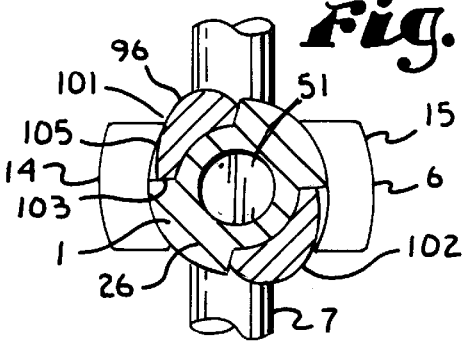
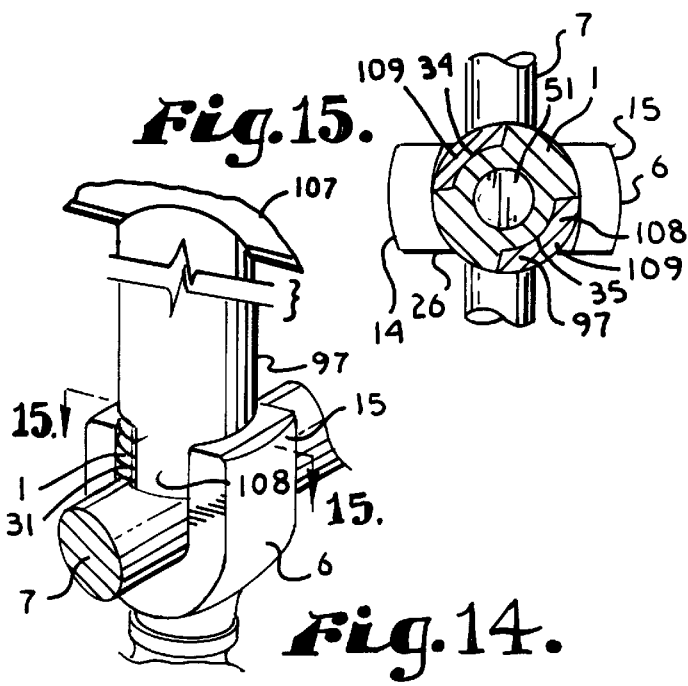

CLOSURE FOR OPEN ENDED MEDICAL IMPLANT AND REMOVAL TOOL

BACKGROUND OF THE INVENTION

The present invention is directed to a closure for use in conjunction with open ended medical implants, such as bone screws, hooks and the like that are used in certain types of spinal surgery. The purpose for the closure is to capture a rod member within the head of the implant and to also lock the captured rod member in position relative to the implant so that the two do not move rotationally or axially with respect to one another.

Medical implants such as bone screws and hooks are used in many types of spinal surgery wherein a structure is built about and within the spine to provide support or strength to diseased, missing or damaged spinal elements of the patient. The implanted apparatus includes a number of different parts which vary with each patient and that are linked together to form a stable support system. For example, bone screws are typically threadably mounted in the bones and have heads that receive rods or similarly shaped connectors that join other bone screws or other elements of the system together. Bone screws of this type may have either closed heads wherein a rod is threaded into the head from the side or an open head wherein a rod is laid in a channel formed in the head. The later type of bone screws are referred to as open ended bone screws. Such open ended bone screws are favored in many types of spinal surgery, since a rod does not have to be threaded through the bone screw which is difficult to do in the tight space provided and because the spine curves making insertion of a rod that follows the spinal curvature very difficult. On the other hand, the open ended bone screws allow the rod to be laid or drawn into the open channel of the head which greatly simplifies installation in comparison to threading the rod through a head of the bone screw.

While open ended medical implants such as bone screws, hooks and the like are often easier to use in comparison to closed end implants of the same type, the open ended implants do have associated problems. In particular, in open headed implant systems it is extremely important that there be no slippage or relative movement between the connecting rods and the implants, such as bone screws, to which the rods are joined. The rods in this case are usually not linear, but are curved to follow the curvature of the spine. If the rod is allowed to slip either axially or rotate within the bone screw or other connector to which the rod is secured, at a minimum the effectiveness of the implant is decreased and it is possible that the patient could be severely injured. Consequently, it is extremely important to secure the rod to the bone screw or other connector so that no slippage occurs. In some of the prior art devices, open headed implants, which typically have a pair of spaced arms, have been internally threaded and have received a threaded plug between the arms, which plug is designed to abut against the rod under torque and both capture the rod in the head and lock the rod into place.

The plug of the prior art has an outer cylindrical surface that is threaded and is received in the threads of the arms. In order to do this the plug has a comparatively large diameter so that the plug extends out sideways relative to the bone screw or the like or the bone screw must be made wider than necessary. That is, the plug makes the overall implant wider than is necessary. This presents problems to the surgeon installing the system, as space is very limited along the rods in many situations and there is not enough room for all of the total system structure to attach to the rods or, if there is sufficient room for attachment of elements, then there may be insufficient room for the surgeon to manipulate the rod by use of benders to shape the rod to conform to the proper spinal curvature, as is required in many of the surgeries using these devices. It is also noted that other prior art devices have a ring that goes around the outside of the arms. Such a ring is very bulky, taking up a great amount of space along the rods to which the implant is joined. Consequently, it is very desirable to eliminate this side to side extension of the closure along the axis of the rod. That is, it is desirable that the implant and closure both have a low side to side profile.

Secondly, as has been mentioned above, the rods are typically bent throughout the length thereof, such that the rods follow the curvature of the spine. Because of this, the rods seat in the open head of the bone screws and other implants in such a manner that the rod has curvature associated with it, even within the head. When plugs of the prior art seat against the rod, typically the rod is bowed so that the rod engages the plug only at the radially outer edges thereof on both sides. The plug is then torqued against the rod to tighten it down against the seat in the bone screw channel, but it is quite difficult to tighten the rod sufficiently so that the portion of the rod within the head has no curvature after tightening. Subsequently, during use of the device, the rod may be flexed or bent by activity of the person, especially greater activity than normal, such as occurs in an accident or the like, and the remaining curvature of the rod flexes somewhat, thereby loosening the plug. When this occurs, the rod may slip axially or rotate relative to the implant and/or the plug may become loosened and work out of the implant. Both of these situations are very undesirable.

Therefore, there is a need to provide a closure for bone screws and other medical implants having an open head such that the closure has both a relatively thin profile along the axis of the rod or the like and also where the closure has a mechanism whereby the rod can be locked centrally opposite the seat to prevent the rod from becoming loosened should the rod flex during usage.

Further, it is sometimes necessary to remove the bone screw closures after being installed. Because of the high torque applied to the closure and because of the relative smallness of the parts, it is often difficult to acquire sufficient purchase to rotate and remove the closure. Therefore, a removable closure and tools for removing the closures are also desired.

SUMMARY OF THE INVENTION

A closure is provided for use in conjunction with open headed medical implants, such as bone screws and hooks, which receive rods and other structure for interconnecting with various parts of an overall system. The closure is bow-tie-shaped with opposed cylindrical sectors that are radially outwardly threaded and that are joined by generally curved walls having a reduced radius in comparison to the cylindrical sectors. The threads on the cylindrical sectors are sized and shaped to mate with the threads on internal surfaces of arms of the implants. The closure also includes a central passthrough threaded bore that is coaxially located with respect to the closure.

A set screw having a base with a radially outwardly threaded surface and a head is threadably mounted in the bore during installation of the closure. The set screw includes a point that extends from the closure bore when fully installed so as to engage a rod member located in the head of the implant. The set screw may be of a break-off head variety or may retain its head after installation. Also the set screw may be designed to rotate with the closure during installation or independently of the closure. In one embodiment the set screw is designed to extend entirely through the bore of the closure during installation and engage a rod in an implant head under torque until the head of the set screw breaks away at a predetermined torque. In such an embodiment the closure functions to capture the rod in the head and the set screw functions to lock the rod in place relative to the head of the implant.

A set of tools is also provided for installation of the closure since the closure has discontinuous threads thereon. The installation tool includes a handle for rotating and a head that has a channel for receiving the closure. The head also has a pair of wings on either side of the channel which are radially outwardly threaded and positioned so as to mate with the closure such that the threads on the closure and the threads on the wings form a generally continuous thread that may be utilized advantageously to mount the closure in the head of the implant. A second tool including a shaft with a threaded tip may also be mounted in the bore of the closure during installation to allow the installer to better grip the closure.

A set of removal tools is also provided. A first removal tool includes a turning handle and a head that receives the closure. The head includes outer surfaces that are of non-uniform radius so as to present a cam surface that is operably wedged against the implant arms to inelastically spread the arms, and thereby loosen the closure. The second tool is similar, but with a head having wings that are uniform in radius and thickness and non-threaded that allow rotation of the closure in the implant after it is loosened.

OBJECTS AND ADVANTAGES OF THE INVENTION

Therefore, the objects of the present invention are: to provide an overall medical implant system wherein the system includes various bone screws, hooks and the like with open heads that are joined with a series of rod-like structures by use of a closure in accordance with the present invention; to provide such a closure which is relatively thin in profile along the axes of the rods with which it is utilized; to provide such a closure which is bow-tie-shaped and includes a pair of cylindrical sectors that are opposed to one another and which are externally threaded so that the closure is only partially threaded and such that the thread is discontinuous between the sectors, but in such a way as to threadably mate with threads on internal surfaces of arms of open headed implants; to provide such a closure which includes a central passthrough and threaded bore; to provide such a closure with such a bore in conjunction with a threaded set screw received in the bore and passing at least partially through the bore during installation; to provide such a closure wherein the closure captures a rod member within a head of an implant and wherein the set screw locks the rod member in place relative to the implant head to prevent rotation or axial relative movement of the rod member in relation to the head; to provide such a closure having a relatively thin profile upon installation; to provide a set of tools to be used in conjunction with installation of the closure; to provide such tools including a closure installation tool having a head that receives the closure and a pair of wings that extend outwardly on either side of the closure with threads on outer surfaces of the wings that compliment threads on the closure so as to provide, when joined, a generally continuous thread for use in installation of the closure; to provide removal tools, especially a tool that operably wedges apart implant arms to loosen a closure therein, to aid in removal in the closure should removal be necessary; to provide such an overall system and, especially, a closure that is relatively easy to use, economical to produce and especially well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a closure in accordance with the present invention.

FIG. 2 is a top plan view of the closure.

FIG. 3 is an exploded side elevational view of a bone screw, the closure on a reduced scale and a pair of tools utilized in installation of the closure in the bone screw.

FIG. 4 is a perspective view of the closure and a fragmentary view of the closure installation tools just prior to joining together thereof.

FIG. 5 is a side elevational view of a medical implant system including the bone screw, a rod and the closure with the closure installing tools thereon and with the closure being installed in a head of the bone screw, with portions broken away to show detail thereof.

FIG. 6 is a fragmentary side elevational view of the bone screw mounted in a vertebra and with the closure capturing a rod therein and still further with a set screw being installed in the closure with a torquing tool.

FIG. 7 is a side elevational view of the bone screw, the rod and the closure of FIG. 6 with a head of the set screw separated from a base thereof subsequent to torquing of the set screw, and with portions broken away to show detail thereof.

FIG. 8 is a cross-sectional view of the implant, the rod, the closure and the base of the set screw, taken along line 8—8 of FIG. 7.

FIG. 9 is a cross-sectional view of the vertebra, the bone screw, the rod, the closure and set screw, taken along line 9—9 of FIG. 8.

FIG. 10 is a partially exploded perspective and fragmentary view of the bone screw, the rod, the closure and a first closure removal tool prior to installation on the closure.

FIG. 11 is a perspective view similar to FIG. 10 with the first closure removal tool positioned on the closure.

FIG. 12 is a cross-sectional view of the bone screw, the closure and the first closure removal tool just prior to use of the first closure tool.

FIG. 13 is a cross-sectional view of the bone screw, the closure and the first closure removal tool similar to FIG. 12 at the end of use of the first closure removal tool to spread arms of the bone screw, FIG. 14 is a fragmentary perspective view of the bone screw, the closure and a second closure removal tool.

FIG. 15 is a cross-sectional view of the bone screw, the closure and the second closure removal tool, taken along line 15—15 of FIG. 14.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally indicates a closure in accordance with the present invention. The closure 1 is utilized in conjunction with a bone screw 6 that receives a rod 7 and is implanted in a vertebra 8 of a patient's spine. The closure 1 is locked with respect to the bone screw 6 by a set screw 9.

The bone screw 6 is conventionally referred to as an open headed bone screw having a threaded shank 11 that is screwed into a patient's vertebra 8 and a head 12. The bone screw head 12 is bifurcated with a pair of upstanding and spaced arms 14 and 15 forming a channel 16 therebetween with a seat 17 at the bottom of the channel 16.

Radially inward and facing surfaces 20 and 21 of the arms 14 and 15 respectively are threaded with a thread that is discontinuous between the surfaces 20 and 21. Use of the term discontinuous here means that the threads on the two surfaces 20 and 21 are substantially spaced from each other. The closure 1 of the present invention may be used in conjunction with any of a number of different types of open headed implants, including the illustrated bone screw 6, hooks or the like which are conventionally used in spinal surgery.

The rod 7 is circular in cross section and elongate, although it is foreseen that rods of other cross section including square may be used with the invention. The rod 7 may also be smooth surfaced or knurled. The rod 7 illustrated in the figures is somewhat curved so as to be upwardly concave when viewed from the side, such as in FIG. 5 or 9. Because the rod 7 is curved, it often does not lie flat in the seat 17, but rather has a primary point of contact 23 that engages the seat 17. In certain embodiments, the rod may engage the seat 17 at more than one location. It is also seen that in accordance with the present invention the closure 1 could be used in conjunction with other rod-like connector structures to maintain such structures in the head of the bone screw.

The closure 1 has a plug or body 26 that is bow tie-shaped when viewed from above or below having a pair of generally equal and opposed cylindrical sections 28 and 29 on either end thereof. Each of the cylindrical sectors 28 and 29 have radially outward surfaces 31 and 32 respectively that are threaded. The threads of the surfaces 31 and 32 are discontinuous with respect to one another with substantial spacing therebetween, such that there is no continuous thread associated with the exterior of the closure 1 itself which extends entirely about the closure 1. In the illustrated embodiment the threads associated with each sector 28 and 29 extend approximately one quarter of the way around the closure 1.

Joining the curved surfaces 31 and 32 are a pair of generally curved surfaces 34 and 35 that are formed by reducing the outer radius of the closure 1 in the region of the surfaces 34 and 35. End walls 36 join the surfaces 34 and 35 with the surfaces 31 and 32. The closure 1 also has a generally flat upper surface 37 and a flat lower surface 38 which are perpendicular with respect to an axis of rotation A of the closure 1. The threads of the curved outward surfaces 31 and 32 are threadably mateable with the threads on the arm surfaces 20 and 21 respectively except that due to the discontinuities it is very difficult to do so without the assistance of the tool described below.

The closure 1 includes a central bore 47 that is coaxial with the axis A of rotation of the closure 1 and that is internally threaded. The bore 47 passes entirely through the closure 1 and extends between the upper surface 37 and lower surface 38.

The set screw 9 has a base 51 and a head 52. The base 51 has a radially outward surface 54 that is threaded so as to be mateable with the thread in the bore 47. The base 51 also has a lower and outwardly projecting point 56 that during and after installation is coaxial with the axis A. The set screw base 51 and head 52 are joined by a break-away region 58, such that the base 51 breaks away from the head 52, when a predetermined torque is applied to the set screw 9, such as is illustrated in FIG. 7. The head 52 includes a grippable surface 61 having a number of polyhedrally arranged faces for gripping by a tool described below, here in a hexagon configuration.

A closure installation tool 66 and a closure holding tool 67 are provided for installing the closure 1. The closure installation tool 66 includes a T-shaped handle 70 and a head 71. A bore 72 runs through the interior of the handle 70 and head 71 for receiving the holding tool 67 and is sized to slidingly receive the holding tool 67 therein.

The head 71 includes a channel 74 sized and shaped to snugly receive the closure 1. FIG. 4 shows the closure 1 just prior to being received in the tool head 71 and FIG. 5 shows the closure 1 received in the tool channel 74. The head 71 also includes a pair of wings 75 and 76 that are positioned on opposite sides of the channel 74. The wings 75 and 76 are formed as fragments of an externally threaded cylindrical ring having a uniform thickness that is equal in width to the difference between the radius of the closure outer curved surfaces 31 and 32 and the closure inner curved surfaces 34 and 35. The wings 75 and 76 also have the same arc as the surfaces 34 and 35 so as to fit snugly therewith and extend generally along the length thereof when mated.

An outer surface 78 and 79 of each wing respectively is threaded and the wings 75 and 76 are sized and shaped such that the threads on the surfaces 78 and 79 compliment and generally complete the threads on the closure surfaces 31 and 32, so that the threads on the radially outward portions of the closure 1 are thereby completed and made generally sufficiently continuous by installation of the closure installation tool 66 on the closure 1 to mount the closure 1 in the head 12. In this manner the closure 1 can be easily screwed into the bone screw head 12 between the arms 14 and 15.

The closure 1 and the installation tool 66 may include markings or structural elements to insure that the closure 1 is properly aligned with the tool 66 and that the threads of the tool 66 are positioned on the correct sides of the closure 1, since the threads on opposite sides are not interchangeable.

The holding tool 67 includes a shank 86 joined to a threaded tip 87 at a shoulder 89 and a turning knob 88 opposite the tip 87. The tip 87 is sized and shaped to be threadably received in the closure bore 47. In particular, the holding tool 67 is slidably inserted through the closure installation tool bore 72, as is seen in FIG. 4 and secured to the closure 1, so as to hold the closure 1 in the closure installation tool channel 74 and such that the threaded outer surfaces 78 and 79 of the closure tool 66 substantially completes the threads on the exterior of the closure 1, FIG. 5. The closure 1 is then threaded into the bone screw head 12, as is also seen in FIG. 5. FIG. 5 shows this process near the end of the installation of the closure 1.

Normally, the closure 1 is not torqued tightly against the rod 7, but is mainly used to capture the rod 7 within the head 12. It is possible for the closure 1 to be tightened tightly to lock the rod 7 and bone screw 6 together in some embodiments, but that is normally the purpose of the set screw 9.

Once the closure 1 is installed, as is seen in FIG. 5, the tools 66 and 67 are removed and the set screw 9 is inserted into the bore 47. A third tool 91 for rotating and torquing is then utilized to rotate the set screw 9. The torquing tool 91 includes a turning handle 93 and a socket-type head 94 that is mateable with the set screw grippable surface 61 to allow torque to be applied to the set screw 9 by turning the tool 91. Normally the set screw 9 would be torqued to a torque sufficient to lock the rod 7 relative to the remainder of the bone screw 6. For example, the set screw 9 may be torqued to 100 inch pounds of torque, although the exact torque may vary with the particular procedure and purpose.

In the illustrated embodiment the set screw 9 is a breakaway head type set screw wherein the head 52 breaks away from the base 51 at a preselected torque. This is seen in FIG. 7. Once the head 52 breaks away from the base 51, the installation is considered to be complete. Preferably, the base 51 includes the point 56 that engages the rod 7. Also preferably the point 56 engages the rod 7 opposite the point of contact 23 of the rod with the seat 17, as is seen in FIG. 9.

It is foreseen that a non-breakaway head type screw may also be used in conjunction with the invention, but a breakaway head set screw provides a lower profile to the completed implant system. The set screw base 52 may also include one or more bores or the like (not shown) to allow the base 51 to be removed after the head 52 is broken away.

It is sometimes necessary to remove the closure 1 after it has been installed in a bone screw 6, such as is shown in FIGS. 8 and 9. Because of the high torque applied to the overall closure 1 and set screw 5 and because the various parts are relatively small in size, it is sometimes quite difficult to remove the closure 1 should it be necessary because of implant failure, desire to rearrange the implant, or the like.

A pair of removal tools, including a first removal tool 96 and a second tool 97 are provided for use in removing the closure 1 from the bone screw 6. The first removal tool 96 includes a T-shaped handle 99 and a head 100. The head 100 includes a pair of wing shaped wedge elements 101 and 102. The elements 101 and 102 are asymmetrical and of non-uniform radius. The elements 101 and 102 have a first end 103 that is at least as small in radius as the difference between the closure surfaces 31 and 32 as compared to the surfaces 34 and 35. Each wedge element 101 and 102 also includes a larger central portion 104 that is substantially larger in cross-section than the difference between the closure surfaces 31 and 32 as compared to the surfaces 34 and 35. The first end 103 and larger center portion 104 are connected by a curved surface 105 that effectively forms a cam.

When installed on the closure 1, as is shown in FIG. 11, the first removal tool is rotated so as to urge the curved surface 105 of each of the wedge elements 101 and 102 against respective bone screw arms 14 and 15. This effectively biases the arms 14 and 15 outwardly in a non-elastic manner so as to spread the arms 14 and 15 somewhat. This also has the effect of loosening the closure 1 within the arms 14 and 15 and partially turning the closure 1 with respect to the bone screw 6, such as is shown in FIG. 13. The first removal tool 96 is then removed from the closure 1.

The second removal tool 97 includes a T-shaped handle 107 ending in a head 108. The head 108 includes a pair of unthreaded counterparts that are partial ring shaped of uniform radius and designed and shaped to fit within the space provided by the difference in radius between the closure surfaces 31 and 32 as compared to the surfaces 34 and 35. The procedure of installing the tool 97 is shown in FIGS. 14 and 15. The closure 1 can then be easily rotated so that the threads of the cylindrical sections 28 and 29 separate from the threads of the bone screw arms 14 and 15, thereby allowing the closure 1 to be removed from the bone screw 6.

The term "continuous" when used herein in conjunction with the term "thread" is meant to describe a thread that is sufficiently complete to allow the structure to which the thread is attached to be readily screwed into a full or partial receiving thread and may include small or slight gaps.

It is to be understood that while certain forms of the present invention have been illustrated and described herein, it is not to be limited to the specific forms or arrangement of parts described and shown.

What is claimed and desired to be secured by Letters Patent is as follows:

1. A closure for an open ended medical implant having a pair of spaced and internally threaded arms; said closure comprising:
    a) a closure body having a thread on a radially outward facing surface; said body thread sized and located to be adapted to mate with internal threads on the implant arms;
    b) said body having opposed equal cylindrical segments such that the body thread is discontinuous; said segments being connected by a radiused joining surface having a radius that is less than a radius associated with said segments;
    c) said body having a central threaded bore; and
    d) a threaded set screw sized and shaped to be received in said threaded bore in use.

2. The closure according to claim 1 wherein:
    a) said body thread is in two opposed equal portions extending in total substantially less than 360° about said body.

3. The closure according to claim 1 wherein:
    a) a said body is bow-tie-shaped when viewed from above.

4. The closure according to claim 1 in combination with a complimenting installation tool; said tool including:
    a) a handle for turning by a user;
    b) a head having a channel sized and shaped to receive said closure body; said head also having a pair of externally threaded wings located on either side of said channel and having threads sized and positioned to compliment threads on said closure to form a continuous thread when joined, such that said closure is screwable into an implant.

5. A closure for an open ended medical implant having a pair of spaced and internally threaded arms; said closure comprising:
    a) a closure body having a partial cylindrical shape with at least one outer portion of uniform radius removed; and b) said body having a radially outer surface that is threaded with a discontinuous thread.

6. The closure according to claim 5 wherein:
a) said body has a pair of equal and opposite outer portions removed.

7. The closure according to claim 6 wherein:
a) said body is bow-tie-shaped.

8. The closure according to claim 7 wherein:
b) said body includes an axially extending pass through and threaded bore; and including
c) a set screw sized and shaped to be operably received in said bore during use.

9. The closure according to claim 8 wherein:
a) said body has a first wall between said bore and each of a pair of outer partial cylindrical shaped and threaded surfaces that is of a uniform first thickness and a second wall between said bore and each of a pair of curved walls between said threaded surfaces that are of a uniform second thickness that is less than said first thickness.

10. A closure for an open ended medical implant; said closure comprising;
b) a closure body having a pair of opposed cylindrical sectors with each of said sectors having radially outward curved surfaces with a first radius and with threads thereon sized and shaped to threadably mate with threads of the medical implant; said sector threads being discontinuous with each other; said sectors being joined by curved walls having an outer second radius that is less than said first radius.

11. The closure according to claim 10 wherein: p1 a) said closure body includes a central pass through and coaxial threaded bore.

12. A medical implant system comprising:
a) a medical implant having an open channel positioned between a pair of arms and being sized and shaped to receive a rod member; said arms being spaced and having threaded internal facing surfaces;
b) a closure body having a radially outward discontinuous threaded surface having a first radius joined by a curved wall having a second radius less than said first radius; said closure body having an axially aligned pass through threaded bore; and
c) a threaded set screw operably received in said bore during installation and being sized and shaped to have a tip extending from said bore when fully installed.

13. The implant system according to claim 12 wherein:
a) said medical implant is a bone screw.

14. The implant system according to claim 12 wherein:
A) said closure body includes two opposed cylindrical sectors with a radially outward surface of each of said sectors being threaded so as to be mateable with the threads of said arm facing surfaces.

15. The implant system according to claim 12 in combination with a closure removal tool; said closure installation tool comprising:
a) a handle for turning by a user;
b) a head coaxially attached to said handle; said head including a channel for receiving said closure and a pair of wings on opposite sides of said channel; each of said wings having a radially outward surface that includes a non-uniform radius cam; each of said wings operably being biasable against the arms of the implant holding said closure so as to spread the arms and loosen said closure for removal.

16. A tool for removing a closure threadedly received between a pair of arms of an implant under torque; said tool comprising:
a) a shaft having an operator turning handle at one end and a head at an opposite end thereof;
b) said head having a channel sized and shaped to receive such a closure and a pair of wings on either side of said channel; and
c) each of said wings having an outer cam surface that has a nonuniform radius, so that said tool is positionable over such a closure and rotatable such that said cam surfaces engage and wedge apart arms of the implant.

* * * * *